US006790372B2

(12) United States Patent
Roy et al.

(10) Patent No.: US 6,790,372 B2
(45) Date of Patent: Sep. 14, 2004

(54) MICRONEEDLE ARRAY MODULE AND METHOD OF FABRICATING THE SAME

(75) Inventors: Shuvo Roy, Cleveland, OH (US); Aaron J. Fleischman, University Heights, OH (US)

(73) Assignee: Cleveland Clinic Foundation, Cleveland, OH (US)

(*) Notice: Subject to any disclaimer, the term of this patent is extended or adjusted under 35 U.S.C. 154(b) by 18 days.

(21) Appl. No.: 10/162,848

(22) Filed: Jun. 5, 2002

(65) Prior Publication Data

US 2002/0155737 A1 Oct. 24, 2002

Related U.S. Application Data

(62) Division of application No. 09/643,103, filed on Aug. 21, 2000, now abandoned.

(51) Int. Cl.$^7$ ................................................. B61C 1/00
(52) U.S. Cl. ............................. 216/10; 216/11; 216/41; 216/49; 216/51; 216/56; 216/66; 216/79; 216/99
(58) Field of Search .................. 216/2, 11, 41, 216/49, 51, 56, 66, 79, 99

(56) References Cited

U.S. PATENT DOCUMENTS

| | | |
|---|---|---|
| 5,112,305 A | 5/1992 | Barath et al. |
| 5,242,397 A | 9/1993 | Barath et al. |
| 5,279,544 A | 1/1994 | Gross et al. |

(List continued on next page.)

OTHER PUBLICATIONS

De Boer, M.J. et al "Micromachining of Buried Micro Channels in Silicon" Journal of Microelectromechanical Systems, 9 (1) 94–103, Mar. 2000.*

U.S. Sherman et al. patent application Publication No. US 2002/0020688 A1, publication date Feb. 21, 2002, entitled Apparatus and Method for Manufacturing an Intracutaneous Microneedle Array.

Bhardwaj et al. "Dry Silicon Etching for Mems", presented at The Symposium on Microstructures and Microfabricated Systems at the Annual Meeting of The Electro Chemical Society. Montreal, Quebec, Canada, May 4–9, 1997.

Primary Examiner—Anita Alanko
(74) Attorney, Agent, or Firm—Tarolli, Sundheim, Covell & Tummino L.L.P.

(57) ABSTRACT

A microneedle array module is disclosed comprising a multiplicity of microneedles affixed to and protruding outwardly from a front surface of a substrate to form the array, each microneedle of the array having a hollow section which extends through its center to an opening in the tip thereof. A method of fabricating the microneedle array module is also disclosed comprising the steps of: providing etch resistant mask layers to one and another opposite surfaces of a substrate to predetermined thicknesses; patterning the etch resistant mask layer of the one surface for outer dimensions of the microneedles of the array; patterning the etch resistant mask layer of the other surface for inner dimensions of the microneedles of the array; etching unmasked portions of the substrate from one and the other surfaces to first and second predetermined depths, respectively; and removing the mask layers from the one and the other surfaces. One embodiment of the method includes the steps of: providing an etch resistant mask layer to the other surface of the substrate to a predetermined thickness; patterning the etch resistant mask layer of the other surface to define a reservoir region in the substrate; and etching away the unmasked reservoir region of the substrate to form a reservoir well in the other surface of the substrate. A layer of material may be provided to the other surface to enclose the reservoir well and a passageway is provided through the layer to the well region.

20 Claims, 5 Drawing Sheets

U.S. PATENT DOCUMENTS

| | | |
|---|---|---|
| 5,354,279 A | 10/1994 | Hofling |
| 5,364,356 A | 11/1994 | Hofling |
| 5,457,041 A | 10/1995 | Ginaven et al. |
| 5,547,467 A | 8/1996 | Pliquett et al. |
| 5,667,491 A | 9/1997 | Pliquett et al. |
| 5,681,281 A | 10/1997 | Vigil et al. |
| 5,713,863 A | 2/1998 | Vigil et al. |
| 5,746,716 A | 5/1998 | Vigil et al. |
| 5,879,326 A | 3/1999 | Godshall et al. |
| 5,911,223 A | 6/1999 | Weaver et al. |
| 6,051,503 A | 4/2000 | Bhardwaj et al. |
| 6,087,197 A | 7/2000 | Eriguchi et al. |
| 6,102,904 A | 8/2000 | Vigil et al. |
| 6,256,533 B1 | 7/2001 | Yuzhakov et al. |
| 6,312,612 B1 * | 11/2001 | Sherman et al. ............... 216/2 |
| 6,331,266 B1 | 12/2001 | Powell et al. |
| 6,334,856 B1 | 1/2002 | Allen et al. |
| 6,379,324 B1 | 4/2002 | Gartstein et al. |

* cited by examiner

MICRONEEDLE ARRAY MODULE AND METHOD OF FABRICATING THE SAME

RELATED APPLICATION

This application is a divisional of U.S. patent application Ser. No. 09/643,103, filed Aug. 21, 2000, now abandoned and assigned to the assignee of the present application.

BACKGROUND OF THE INVENTION

The present invention is related to microelectromechanical systems (MEMS) and the fabrication thereof, in general, and more specifically, to a microneedle array module and its fabrication.

Targeted drug delivery or the application of a high concentration of one or more drugs to a specific target area within the body has become of paramount importance to the fight against tumors, restentosis and similar life threatening medical conditions. Generally, these target areas are reachable through the walls of the blood vessels of the body. Present systems use a catheter with an imaging device to locate the target area. Once located, a specific drug or drugs are delivered to the targeted vessel wall area. But, this process has posed serious problems.

One approach provides a drug inside a perforated balloon at the end of the catheter. When the balloon reaches the target area, it is inflated causing the drug to be released through the perforations of the balloon locally around the targeted walls of the vessel. This perfusion of the drug at the surface of the vessel walls relies heavily on the drug being absorbed quickly and efficiently by the vessel walls at the target area. However, in some cases the drug may not be absorbed by the vessel walls very effectively. In these cases, the drug may be caused to move downstream with the blood stream which may cause adverse medical effects to portions of the body not intended to receive the drugs, especially at such high concentrations. The drugs may also be diluted in this delivery process and lose their effectiveness. In any event, these relatively expensive drugs may not be achieving their intended purpose.

Some recent drug delivery systems, like those proposed in the U.S. Pat. Nos. 5,112,305; 5,242,397; 5,681,281; 5,713,863 and 5,746,716, for example, provide for a studded balloon catheter. The balloon or portions thereof contain the drug or drugs to be delivered to the target area. When the balloon reaches the target area, it is inflated causing the studs to press against the vessel walls. The drug is then forced from the balloon through the studs into the surface of the vessel walls. However, the stud protrusions of the balloon are not needles and thus, are not very efficient at puncturing the vessel walls, especially at depths adequate for injecting the specific drug.

What is needed for effective drug delivery is an array of microneedles of sufficient length which may be deployed to the target site within the body and adequately penetrate the vessel walls thereat to permit the drug to effectively act on the target area at the high concentrations intended. Such an array structure may also be used transdermally for drug delivery as well.

SUMMARY OF THE INVENTION

In accordance with one aspect of the present invention, a microneedle array module comprises a multiplicity of microneedles affixed to and protruding outwardly from a front surface of a substrate to form the array, each microneedle of the array having a hollow section which extends through its center to an opening in the tip thereof. The substrate includes an array of holes which align with the hollow sections of the microneedles and extend through the substrate to a back surface thereof, whereby a liquid applied to the back surface of the substrate may be forced through the holes in the substrate and out through the tips of the microneedle array thereof. In one embodiment, the substrate includes a reservoir well in the back surface thereof. The well extends over the array of holes in the back surface and may be covered by a layer of material which is affixed to the back surface peripheral the well, the layer including an interconnecting passageway to the well.

In accordance with another aspect of the present invention, a method of fabricating a microneedle array module comprises the steps of: providing etch resistant mask layers to one and another opposite surfaces of a substrate to predetermined thicknesses; patterning the etch resistant mask layer of the one surface for outer dimensions of the microneedles of the array; patterning the etch resistant mask layer of the other surface for inner dimensions of the microneedles of the array; etching unmasked portions of the substrate from one and the other surfaces to first and second predetermined depths, respectively; and removing the mask layers from the one and the other surfaces. One embodiment of the method includes the steps of: providing an etch resistant mask layer to the other surface of the substrate to a predetermined thickness; patterning the etch resistant mask layer of the other surface to define a reservoir region in the substrate; and etching away the unmasked reservoir region of the substrate to form a reservoir well in the other surface of the substrate. A layer of material may be provided to the other surface to enclose the reservoir well and a passageway is provided through said layer to the well region.

DETAILED DESCRIPTION OF THE INVENTION

FIGS. 1A–1H and FIGS. 2A–2G are illustrations of two exemplary methods of fabricating a microneedle array module. FIGS. 1G and 2F depict cross-sectional views of alternative embodiments of microneedle array structures having microneedles cylindrical in shape and conical in shape, respectively. The structures of FIGS. 1G and 2F result from their respective fabrication methods. FIGS. 3A and 3B depict two three-dimensional perspectives of the exemplary resulting microneedle array module shown in the cross-sectional view of FIG. 2F. FIGS. 1H and 2G provide cross sectional views of further embodiments of the array structure in which a reservoir well thereof is covered as will become better understood from the description found herein below.

Figure 1A:
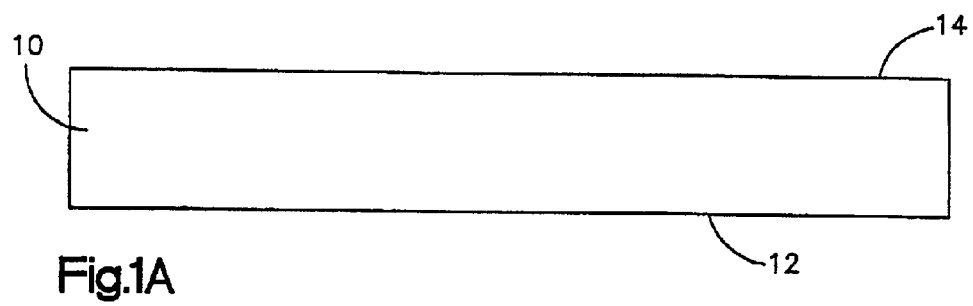
FIGS. 1A–1H are cross-sectional illustrations exemplifying a method of fabricating a microneedle array module in accordance with the present invention.

In FIG. 1A is shown a substrate 10 having a front surface 12 and back surface 14. The substrate 10 may be comprised of Silicon or a glass material, or a form of $SiO_2$, like pyrex, for example, and be on the order of four hundred micrometers (400 µm) thick, for example. In the present embodiment, the substrate 10 is part of a double side polished (100) Silicon wafer that may be on the order of one hundred millimeters (100 mm) in diameter. Next, in the step of FIG. 1B, an etch resistant mask layer 16 is provided to both of the front and back surfaces of the substrate 10. In the present embodiment, the wafer is thermally oxidized to grow a one thousand Angstrom (1000 Å) thick film of $SiO_2$ on both surfaces 12 and 14. The front and back surfaces may also be oxidized by chemically depositing an oxide thereon. In any event, it is further understood that other forms of etch resistant masks may be used such as providing a layer of Silicon Nitride or of a photoresist to the surfaces, for example, without deviating from the principles of the present invention.

Figure 1B:
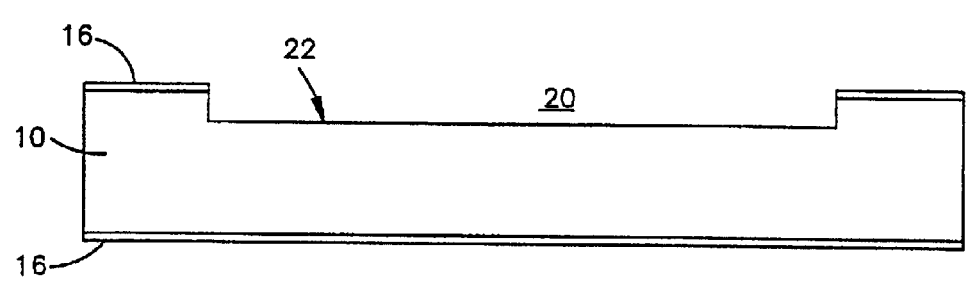
Figure 2A:
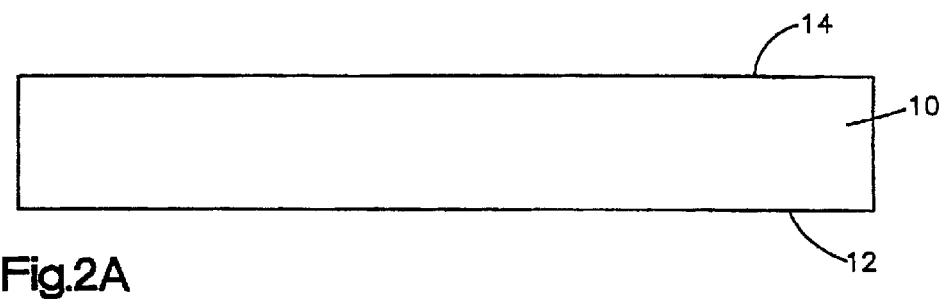
FIGS. 2A–2G are cross-sectional illustrations exemplifying an alternate method of fabricating a microneedle array module.
Figure 2B:
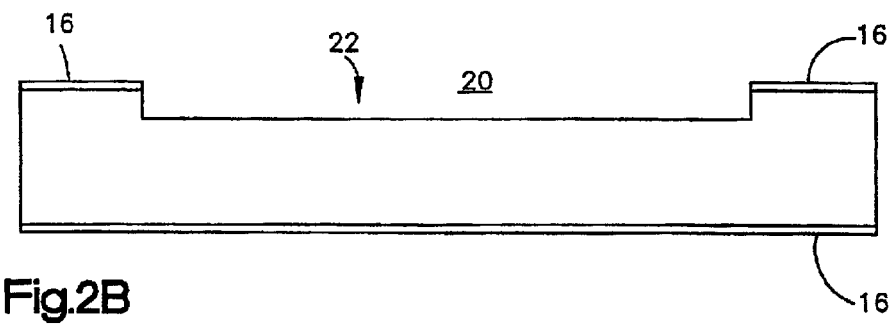
Figure 2C:
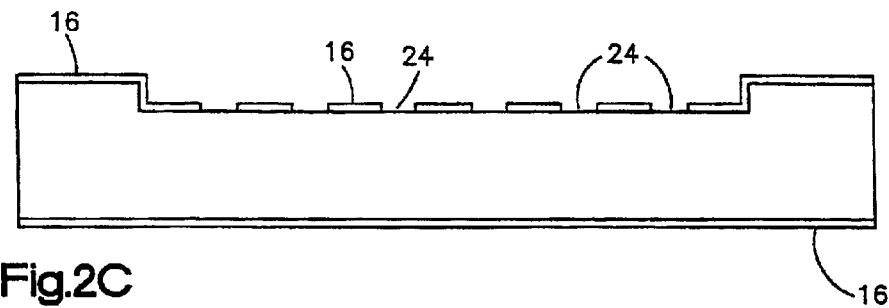
Figure 2D:
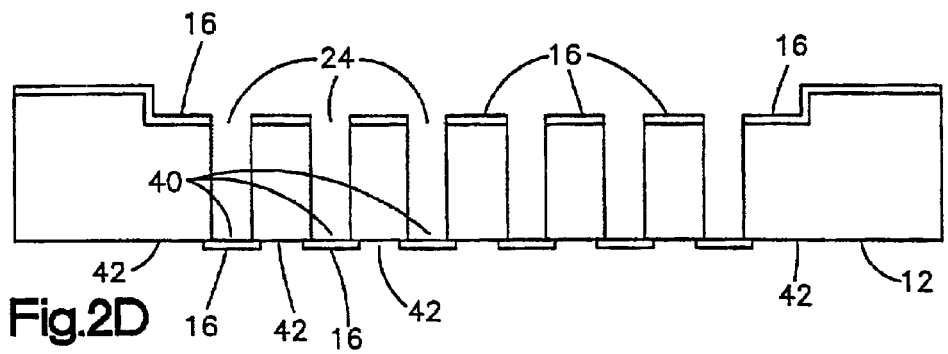

Also, in the step of FIG. 1B, the etch resistant mask of the back surface 14 is patterned using a conventional photolithography process, for example, to define a reservoir region 20 in the substrate 10 and the reservoir pattern of the $SiO_2$ film is etched using buffered hydrofluoric acid (BHF) or fluorocarbon ($CHF_3$)—based reactive ion etching (RIE), for example, to realize an unmasked reservoir region. Next, the unmasked reservoir region 20 of substrate 10 is etched to a depth of approximately 10–20 $\mu$m using a Potassium Hydroxide (KOH) or Silicon Fluoride ($SF_6$)—based RIE, for example, to form a reservoir well 22 in the back surface 14. Subsequently, the etch resistant mask on the back surface 14 is removed using a BHF etch.

Figure 1C:
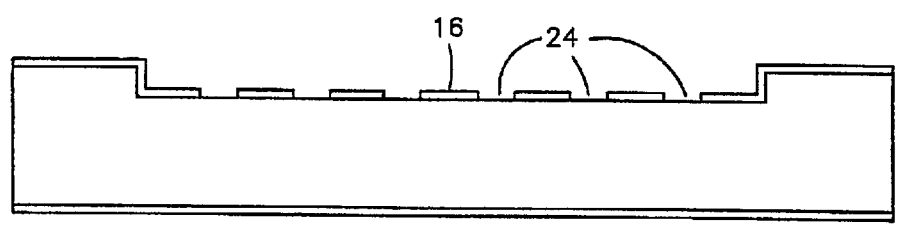
Figure 1D:
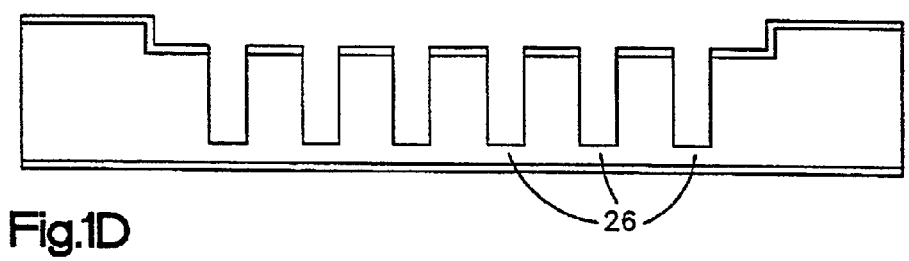

Another etch resistant mask layer 16 is provided over the back surface 14 including the well region 22 to an approximate thickness of 1.5 $\mu$m, for example, using a thermal oxidation process or other process in a similar manner as described above and is patterned using a conventional thick photoresist photolithography and a BHF etch or fluorocarbon-based RIE process to define the inner dimensions or openings of the microneedles of the array, which maybe on the order of 15–20 $\mu$m, for example, as shown in FIG. 1C. In the step of FIG. 1D, the unmasked portions 24 of the back surface 14 including the well or reservoir region 22 are etched to a predetermined depth, say on the order of 350 $\mu$m, for example. In the present embodiment, the substrate is etched anisotropically using a deep reactive ion beam etching (RIE) process, preferably using a Silicon Fluoride ($SF_6$) based ion beam. This etching leaves only thin layers 26 of the substrate relative to the thickness of the substrate. In the present embodiment, these thin layers 26 may be on the order of 40–50 $\mu$m, for example.

Figure 1E:
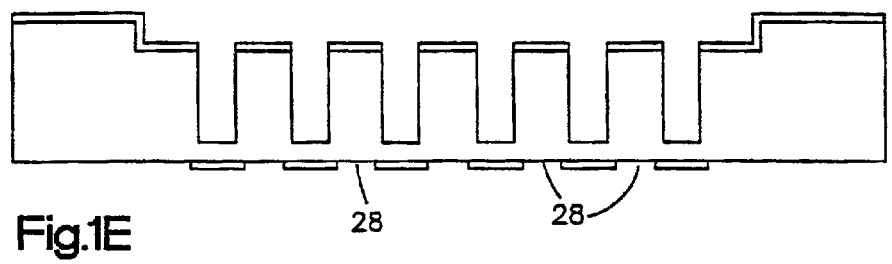
Figure 1F:
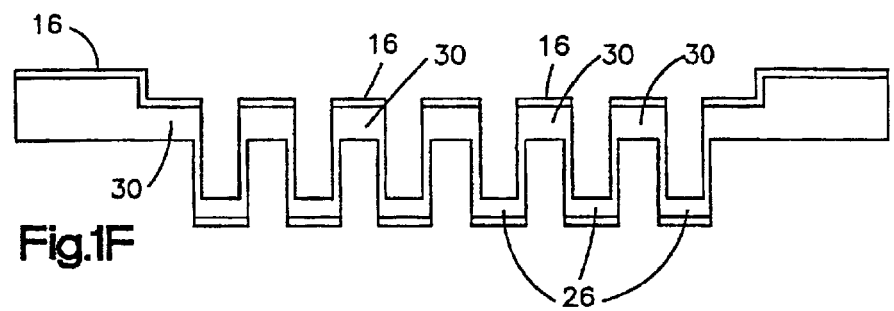
Figure 1G:
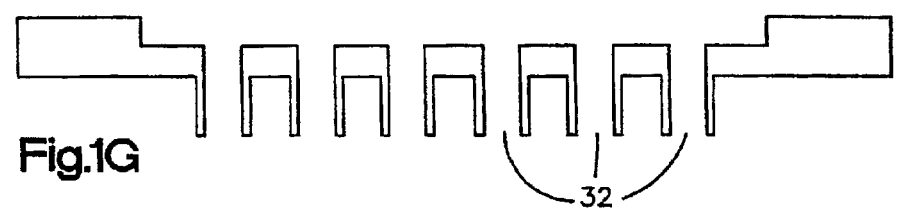
Figure 1H:
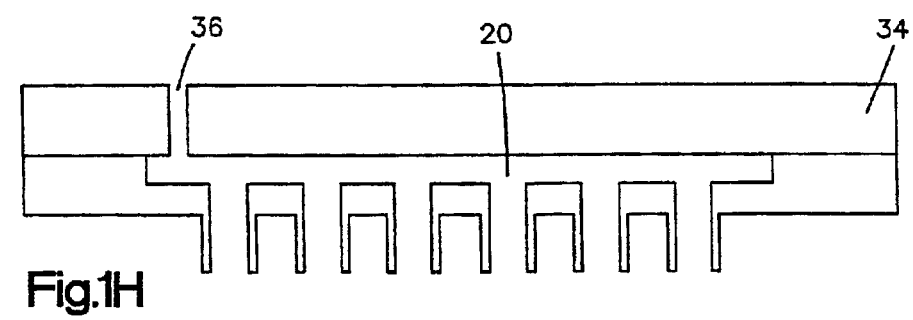

In the step of FIG. 1E, the etch resistant layer 16 of the front surface 12 is patterned, preferably using a conventional thick photoresist photolithography process and fluorocarbon-based RIE, to define the outer dimensions of the microneedles of the array, which may be on the order of 25–30 $\mu$m, for example. The unmasked portions 28 of the substrate 10 are similarly anisotropically etched using the deep RIE process to another predetermined depth leaving substantial layers 30 of substrate 10, say on the order of 80–90 $\mu$m, for example, under the masked layer patterns 16 at the back surface 14 as shown in FIG. 1F. Thereafter, the etch resistant masks 16 are removed from the front and back surfaces 12 and 14, respectively, preferably using a buffered hydrofluoric acid wash. Next, the thin layers of unetched substrate 26 are removed, preferably by anisotropic etching, from the front surface 12 using the deep without any etch mask to provide openings 32 for the tips of the microneedles of the array as shown in FIG. 1G. Finally, as shown in FIG. 1H, a layer of material 34, preferably a Pyrex wafer, is provided over the back surface 14 about the periphery of the well region 20 to enclose the reservoir. However, it is understood that this layer of material 34 is not limited to pyrex, but rather may include at least one material selected from the group of silicon, ceramic, plastic and some form of $SiO_2$, for example. A passageway 36 is provided through said layer 34 to the well region 20. In the present embodiment, the pyrex layer 34 is anodically bonded to the surface 14 and the passageways 36 are created by ultrasonic drilling through the pyrex layer 34. It is further understood that other standard methodologies to attaching the enclosing wafer and creating passageways therein may also be utilized without deviating from the principles of the present invention.

The resulting fabricated microneedles of the array protruding from the remaining layer 30 of the substrate 10 are cylindrical in shape and substantially the same in dimension, having approximately 300 $\mu$m in height, for example. However, it is understood that the foregoing described fabrication process may produce microneedles having height dimensions that are greater than the dimension of the remaining thickness 30 of the substrate material. In addition, the fabrication process described above may be applied to starting substrates of different thicknesses to produce protruding dimensions of the microneedles that may range from 50–2000 $\mu$m, for example. Accordingly, the resulting microneedle array module comprises: a substrate having front and back surfaces; and a multiplicity of microneedles that protrude outwardly from the front surface to form the array, each microneedle including a hollow section which extends through its center to an opening in the tip thereof. The substrate includes an array of holes which align with the hollow sections of the microneedles and extend to the back surface as shown in FIG. 1G, whereby a liquid applied to the back surface may be forced through the holes in the substrate and out through the tips of the microneedles of the array. In the present embodiment, the microneedles are fabricated from the substrate and form an integral part thereof. Also, a reservoir well 22 is provided in the back surface and extends over the array of holes in the substrate. A layer of material 34 covering the well 22 is affixed to the back surface peripheral the well region 20 and includes an interconnecting passageway 36 to the well through which liquid may flow.

While the fabrication method described in connection with FIGS. 1A–1H provide microneedles of cylindrical shape. It is understood that such microneedles may also be fabricated in other shapes, like for example in a conical shape. The method of FIGS. 2A–2G illustrate the steps of a method which produce a module having an array of conically shaped needles. In FIGS. 2A–2G, reference numerals for the steps will remain the same as used to describe the method of FIGS. 1A–1H. Referring to FIGS. 2A–2G, the steps of this alternative process remain the same as that described herein above down through FIG. 2D wherein the etch resistant masks 16 of the front and back surfaces are patterned to define the inner and outer dimensions, respectively, of the microneedles of the array. In FIG. 2D, the unmasked portions 24 of the substrate 10 are etched anisotropically using the same or similar deep RIE process to a depth which creates openings 40 under the masks 16 at the front surface 12. These openings 40 form the tips of the microneedles of the array.

Figure 2E:
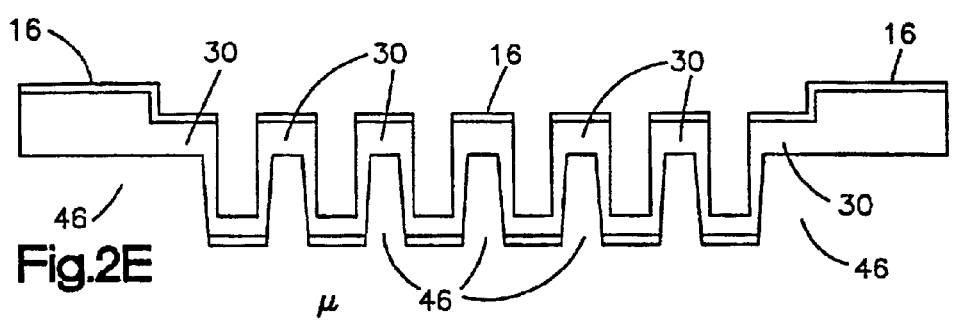
Figure 2F:
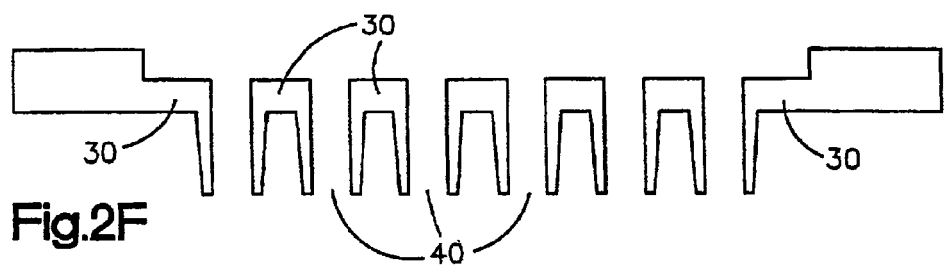
Figure 2G:
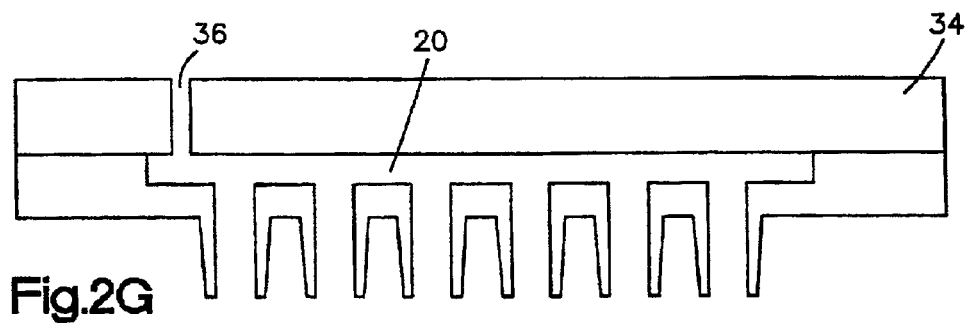
Figure 3A:
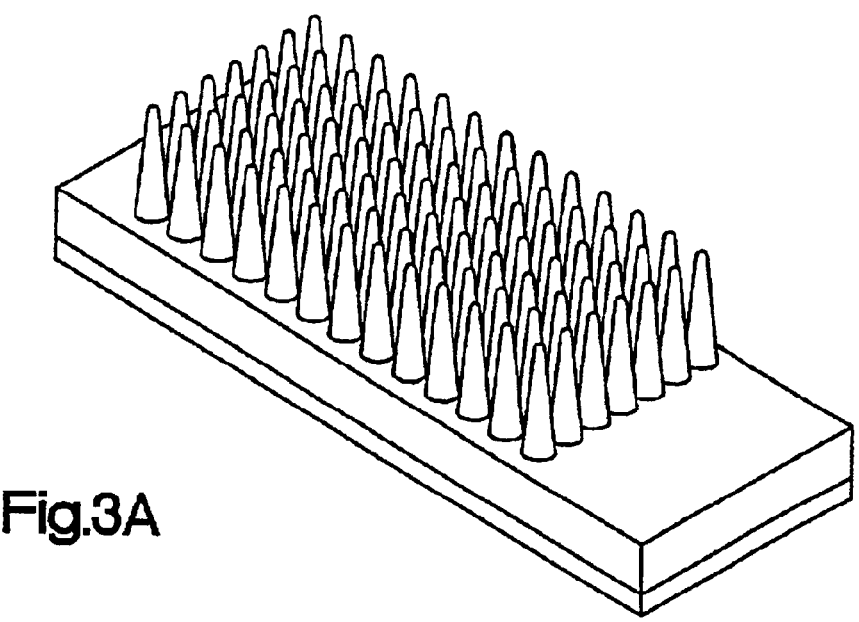
FIGS. 3A and 3B depict two three-dimensional perspectives of an exemplary embodiment of a microneedle array module in accordance with the present invention.
Figure 3B:
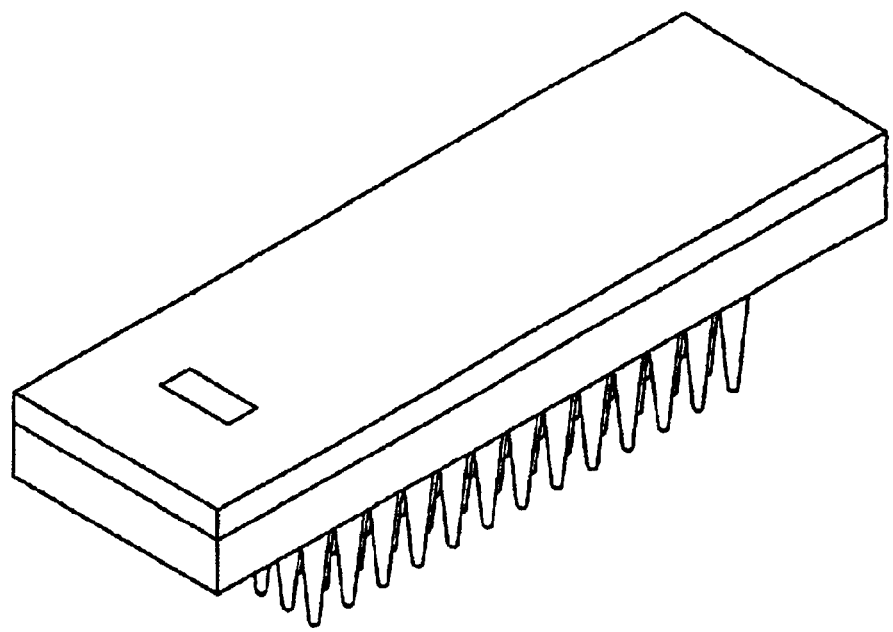

In FIG. 2E, the unmasked portions 42 of the front surface are etched anisotropically using the same or similar deep RIE process controlled to contour the sides of the etched wells 46 in the substrate 10 to form the conical shape of the microneedles. In the present embodiment, process parameters, including gas pressures and voltages, for example, in the deep RIE process are adjusted to control the contour of the etched sidewalls of the microneedles. The paper entitled "Dry Silicon Etching For MEMS" by J Bhardwaj et al., which was presented at the Symposium on Microstructures and Microfabricated Systems at the annual meeting of the Electrochemical Society, Montreal Quebec, Canada, May 4–9, 1997, which is incorporated by reference herein for providing the details of a deep RIE process suitable for use in the fabrication methods. A similar remaining substrate layer 30 is left from the etching process under the masked regions 16 at the back surface 14. Thereafter, the etch resistant patterned masks 16 are removed from the front and back surfaces 12 and 14, respectively, preferably using a BHF etch. Note that the resulting structure depicted in FIG. 2F provides for openings 40 at the tips of the microneedles without further fabrication. In FIG. 2G, the layer 34 is bonded to the back surface 14 to enclose the reservoir region 20, if appropriate, and passageway 36 provided in the same or similar manner as that described in connection with FIG. 1H herein above.

Two three-dimensional views of one embodiment of a microneedle array module is shown in FIGS. 3A and 3B. This exemplary module has outside dimensions of approximately one millimeter (1 mm) by one-half a millimeter (0.5 mm) and includes more than ten rows of microneedles with each row including approximately seven microneedles, for example, to render an array of approximately one-hundred microneedles. An array of holes through the substrate and aligned with the microneedles are shown in the reservoir region. Thus, liquid applied to the reservoir region may be forced through the holes and out of the tips of the microneedles of the array.

While the present invention has been described herein above in connection with one or more embodiments, it is understood that these embodiments are used merely by way of example. Accordingly, the present invention should not be limited to any such embodiments, but rather construed in breadth and broad scope in accordance with the appended claims.

We claim:

1. A method of fabricating a microneedle array module comprising the steps of:
   providing etch resistant mask layers to one and another opposite surfaces of a substrate to predetermined thicknesses;
   patterning the etch resistant mask layer of the one surface for outer dimensions of the microneedles of said array;
   patterning the etch resistant mask layer of the other surface for inner dimensions of the microneedles of said array;
   etching unmasked portions of said substrate from one and the other surfaces to first and second predetermined depths, respectively; and
   removing the mask layers from the one and the other surfaces.

2. The method of claim 1 wherein the step of providing includes oxidizing the surfaces of the substrate to predetermined thicknesses.

3. The method of claim 2 wherein the step of oxidizing includes the step of thermally oxidizing the surfaces.

4. The method of claim 2 wherein the step of oxidizing includes chemically depositing an oxide on the surfaces.

5. The method of claim 1 wherein the step of providing includes the step of providing a mask layer of silicon nitride to the surfaces of the substrate.

6. The method of claim 1 wherein the step of providing includes the step of providing a mask layer of photoresist to the surfaces of the substrate.

7. The method of claim 1 wherein the unmasked portions of the substrate are etched anisotropically.

8. The method of claim 7 wherein the unmasked portions of the substrate are anisotropically etched using a deep reactive ion beam etching (RIE) process.

9. The method of claim 8 wherein the deep RIE process uses a $SF_6$ based ion beam.

10. The method of claim 1 wherein each step of patterning includes the steps of patterning the etch resistant mask layer using a photolithography process.

11. The method of claim 1 wherein the mask layers are removed away using a buffered hydrofluoric acid.

12. The method of claim 1 wherein the mask layers are removed away using a reactive ion etching (RIE) process.

13. The method of claim 12 wherein the mask layers are removed away using a fluorocarbon-based RIE.

14. The method of claim 1 wherein the second predetermined etching depths are greater than the first predetermined etching depths.

15. The method of claim 14 wherein the second etching depths leaving only thin layers of substrate at the one surface relative to the thickness of the substrate; and wherein, the thin layers of unetched substrate portions are etched from the one surface to provide openings for microneedle tips of the array.

16. The method of claim 14 wherein the second etching depths creating openings in the one surface for the microneedle tips of the array.

17. The method of claim 1 including the steps of:
   providing an etch resistant mask layer to the other surface of the substrate to a predetermined thickness;
   patterning the etch resistant mask layer of the other surface to define a reservoir region in the substrate; and
   etching away the unmasked reservoir region of the substrate to form a reservoir well in the other surface of the substrate.

18. The method of claim 17 including the steps of: providing a layer of material to the other surface to enclose the reservoir well; and providing a passageway through said layer to the well region.

19. The method of claim 18 including the reservoir well is enclosed by bonding a layer of material to the other surface.

20. The method of claim 19 wherein the material of the layer bonded to the other surface is selected from the group consisting of a form of $SiO_2$, silicon, ceramic, and plastic.

* * * * *